(12) United States Patent
Deves et al.

(10) Patent No.: US 6,558,625 B1
(45) Date of Patent: May 6, 2003

(54) DISTRIBUTION DEVICE FOR AUTOMATIC CATALYST EVALUATION MULTI-REACTORS

(75) Inventors: Jean-Marie Deves, Vernouillet (FR); Jean-Yves Bernhard, Mennecy (FR); Bernard Chatelain, Jouy le Moutier (FR); Pierre Toutant, Franconville-la Garrenne (FR); José Brandely, Savigny sur Orge (FR); Corinne Guitton, Chatou (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 125 days.

(21) Appl. No.: 09/604,732

(22) Filed: Jun. 28, 2000

(30) Foreign Application Priority Data

Jun. 28, 1999 (FR) .............................. 99 08283

(51) Int. Cl.⁷ .................. G01N 31/12; G01N 33/48; G01N 21/00; G01N 31/22; B01J 19/00
(52) U.S. Cl. .................. 422/78; 422/68.1; 422/58; 422/129; 422/83
(58) Field of Search .................. 422/78, 100, 190, 422/80, 83, 68.1, 109, 130; 73/863.11; 55/302; 518/706; 210/198.2; 137/1, 2, 8; 141/244; 222/1, 3, 4

(56) References Cited

U.S. PATENT DOCUMENTS 4,272,481 A  6/1981 Ahlstrom Jr.
4,779,466 A * 10/1988 Ramsner et al. ......... 73/863.33
5,039,322 A *  8/1991 Holzl ........................ 55/302
5,045,568 A *  9/1991 Quang et al. ............. 518/706
5,192,512 A *  3/1993 Quang et al. ............. 422/190
5,266,270 A * 11/1993 Ajot et al. .................. 422/80
5,770,154 A *  6/1998 Bigeard et al. ............. 422/80
5,777,241 A *  7/1998 Evenson ................. 73/863.11
5,997,819 A * 12/1999 Mougin et al. ............ 422/100
6,148,678 A * 11/2000 Chapman ................ 73/863.11
6,224,762 B1 *  5/2001 Ferschneider et al. ... 210/198.2

FOREIGN PATENT DOCUMENTS

EP      190718       8/1986
EP      243569      11/1987

* cited by examiner

Primary Examiner—Jill Warden
Assistant Examiner—Brian Sines
(74) Attorney, Agent, or Firm—Antonelli, Terry, Stout & Kraus, LLP

(57) ABSTRACT

The present invention relates to a distribution device intended for a gaseous effluent produced by a chemical reaction, comprising at least two inlet ways and two outlet ways. This device comprises at least one closed-loop line divided into four sections by four controlled sealing elements, and each one of said four ways communicates with a single section so that the inlet ways are connected to two opposite sections and said outlet ways are connected to the other two sections.

7 Claims, 6 Drawing Sheets

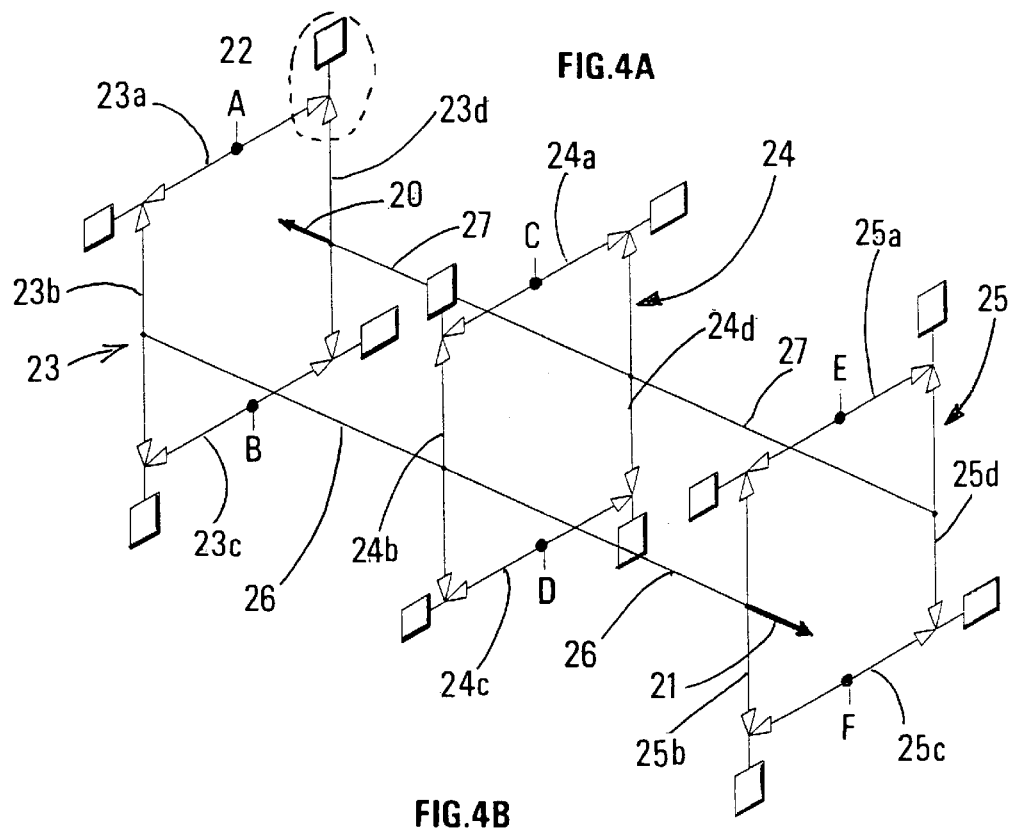

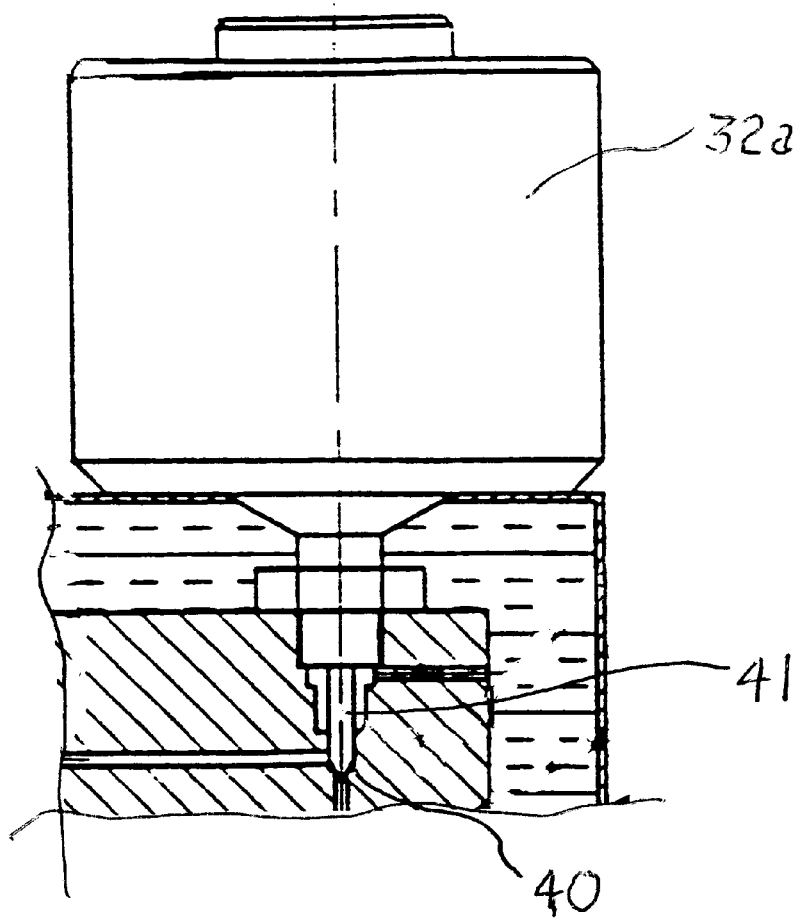

DISTRIBUTION DEVICE FOR AUTOMATIC CATALYST EVALUATION MULTI-REACTORS

FIELD OF THE INVENTION

The present invention relates to a distribution device notably intended for an automatic equipment allowing multi-reactor testing of chemical reactions, possibly in the presence of a catalyst. For this type of equipment to work under high pressure and high temperature conditions, it necessarily comprises a distribution device withstanding these conditions while operating a system intended for in-line analysis of the reaction products. The present invention can be advantageously automated so that the multi-reactors can be used in parallel. Fast and simultaneous evaluation of several sets of operating conditions thus allows acquisition of data on the progress of the reaction and on the performances of solid catalysts.

In-line analysis is possible through precise control of the temperature and of the total and partial pressures of the products coming from the reactors. The distribution device must also allow such control. The elaborate automation of the assembly allows to carry out simultaneous cycles of all the reactors without the operator's intervention.

BACKGROUND OF THE INVENTION

The development of industrial refining and petrochemical processes requires acquisition of data on the chemical reactions that take place. When these reactions are catalyzed, research and development of the catalysts required involve evaluation of the performances thereof. In the laboratory, these data acquisitions and evaluations are performed in pilot plants which reproduce on a small scale the industrial operating conditions.

There are many types of equipments allowing to measure the rate of progress of chemical reactions or the activity of solid catalysts. In the field of petroleum refining and of petrochemistry, the operating conditions under which these measurements are performed are as follows:

pressure ranging between $1.10^5$ and $3.10^7$ Pa, temperature ranging between ambient temperature and 800° C., liquid and/or gaseous reagent flow rates expressed in form of hourly volume flow rate per unit of volume of reactor or catalyst (hourly space velocity) ranging between 0.01 and 100 $h^{-1}$ and by the ratio of the molar flow rate of gas (most often hydrogen) and the liquid reactive hydrocarbon ($H_2$/HC) ranging between 0.01 and 50.

More precise selection of the operating conditions depends on the type of process or of catalyst considered. It can be, for example, one of the following industrial applications: reforming, isomerization, hydrocracking, hydrotreating, selective hydrogenation, conversion of aromatics or oxidation.

Solid catalysts are used as balls, extrudates or powder of variable grain size. The quantities of catalysts used in these pilot plants generally range between some grams and several ten or hundred grams. These quantities are relatively great and they can be a limitation to the use of these pilot plants. In particular, during research or development of a new catalyst, the quantities of solid catalyst available for testing are quite often limited (less than one gram) and there can be a great number of catalytic solid variants. All the available samples are therefore not necessarily tested.

The most isothermal operating conditions possible are sought for the reactors. This is generally obtained by placing the reactor in an oven consisting of several zones whose temperature is independently controlled (U.S. Pat. No. 5,770,154). The dimensions of the reactors also receive particular attention. In particular, the length/diameter ratio of the catalyst bed is most often selected between 50 and 200 so as to ensure proper flow of the reagents and of the products through the catalyst, failing which diffusion or backmixing limiting phenomena disturb measurement of the progress rates and performances of the catalyst.

Catalysts generally require, prior to the reaction stage proper, an activation stage which changes one or more of their constituents into a really active element for catalysis. It may be an oxide reduction in hydrogen in the case of supported metal catalysts or sulfurization in the presence of a sulfur-containing forerunner for catalysts based on metal sulfides. In conventional pilot plants with large dead volumes and a great thermal inertia because of the size of the ovens, this activation stage is generally long (typically of the order of several hours to several ten hours).

The nature of the reagent used (most often a hydrocarbon or a mixture of hydrocarbons) depends on the application considered. It can be a pure hydrocarbon such as, for example, normal hexane, normal heptane or cyclohexane, or more or less heavy or more or less wide petroleum cuts such as, for example, gasolines, gas oils or distillates from crude oil distillation. The quantities of reagent consumed depend of course on the size of the reactor and on the operational time. Most often, however, the performances are calculated from inlet-outlet material balances performed over relatively long periods (some hours to several ten hours). These periods are necessary to allow to collect a sufficient amount (several liters to several ten liters) of products in order to draw up a precise material balance. Using a pure hydrocarbon-containing molecule whose manufacturing cost is high is not always possible under such conditions.

Furthermore, during the period of evaluation of the material balance, which can be long, the catalyst may undergo a certain deactivation. Since the activity of the catalyst is not the same between the beginning and the end of the material balance, the performances calculated in fine only reflect an average behaviour of the catalyst, far from the real evolution of the performances in time.

The effluents coming from the reactor are conventionally separated by expansion and cooling into two phases: liquid and gaseous, whose characteristics and compositions are analyzed separately. These separate separation and analysis operations inevitably lead to product losses which reduce the accuracy of the global material balance. In some cases, analysis of all of the products cannot be carried out at one go with a single chromatographic analyzer. It is then possible to perform an in-line analysis before liquid/gas separation together with an analysis of the gaseous fraction taken after separation. This allows to draw up accurate material balances in this case (U.S. Pat. No. 5,266,270).

Automation of conventional pilot plants remains quite often underdeveloped. The size of these plants and observance of the safety regulations linked with automatic operation make this automation complex and expensive. In particular, the operating conditions determining the severity with which the reaction progresses (temperature or volume flow rate of the reagent) are most often manually adjusted by the plant operator.

To sum up, the conventional pilot plants commonly used for measuring the progress of chemical reactions and the performances of catalysts have a certain number of drawbacks, such as:

the necessity for a large quantity of catalyst and of reagent, the length of the set-up time and the time required for drawing up the material balance required to determine the performances, the performances reflect an average behaviour of the catalyst over a relatively long period, the performance measurement frequency is relatively low, complete operation automation is difficult and expensive.

On account of these drawbacks, conventional pilot plants are not very well suited for fast and precise screening, among many catalytic solids, of the most interesting solids for development of a new catalyst or study of a new reaction.

SUMMARY OF THE INVENTION

The present invention thus relates to a distribution device notably intended for a gaseous effluent produced by a chemical reaction, comprising at least two inlet ways and two outlet ways. The device comprises at least one closed-loop line divided into four sections by four controlled sealing elements, each one of said ways communicates with a single section so that the inlet ways are connected to two opposite sections and said outlet ways are connected to the other two sections.

The device can comprise two closed-loop lines and the outlet ways communicate together two by two so as to form a distribution device with four inlet ways and two outlet ways.

The sealing elements can consist of a conical needle cooperating with a sealed seat.

The sealing elements can be controlled by a pneumatic jack type operator.

The closed-loop line can consist of four rectilinear lines arranged in the shape of a quadrilateral, the sealing elements being substantially located at the four corners of the quadrilateral.

The sealing elements can be suited for an effluent pressure and temperature that can reach 250 b and 400° C. respectively.

The distribution device according to the invention can be applied to an equipment for performing measurements on an effluent resulting from a chemical reaction taking place in a reactor containing a catalyst, and comprising:

at least two reactors, effluent analysis and measuring means, means intended for automatic monitoring and control of the chemical reaction and of the analysis and measurement cycle, the device supplying the analysis and measuring means alternately with the effluents from the two reactors in order to perform analysis and measurement cycles on two reactions progressing in parallel.

The following advantages of the device according to the invention can notably be mentioned:

automatic measurement of the progress of chemical reactions and of catalytic performances in parallel in several reactors, possible control of the partial pressures and temperatures of the effluents in order to allow single and complete analysis without separation into several fractions, selective and frequent measurement of the reaction and catalytic performances, higher performance determination accuracy thanks to the limited dead volumes, complete progress of the operating cycles without the operator's intervention.

BRIEF DESCRIPTION OF THE DRAWINGS

Other features and advantages of the present invention will be clear from reading the description hereafter, given by way of non limitative example, with reference to the accompanying figures wherein:

FIGS. 4a, 4b, 4c, 4d and 4e show the principle and an embodiment of the device according to the invention.

DETAILED DESCRIPTION

Figure 1:
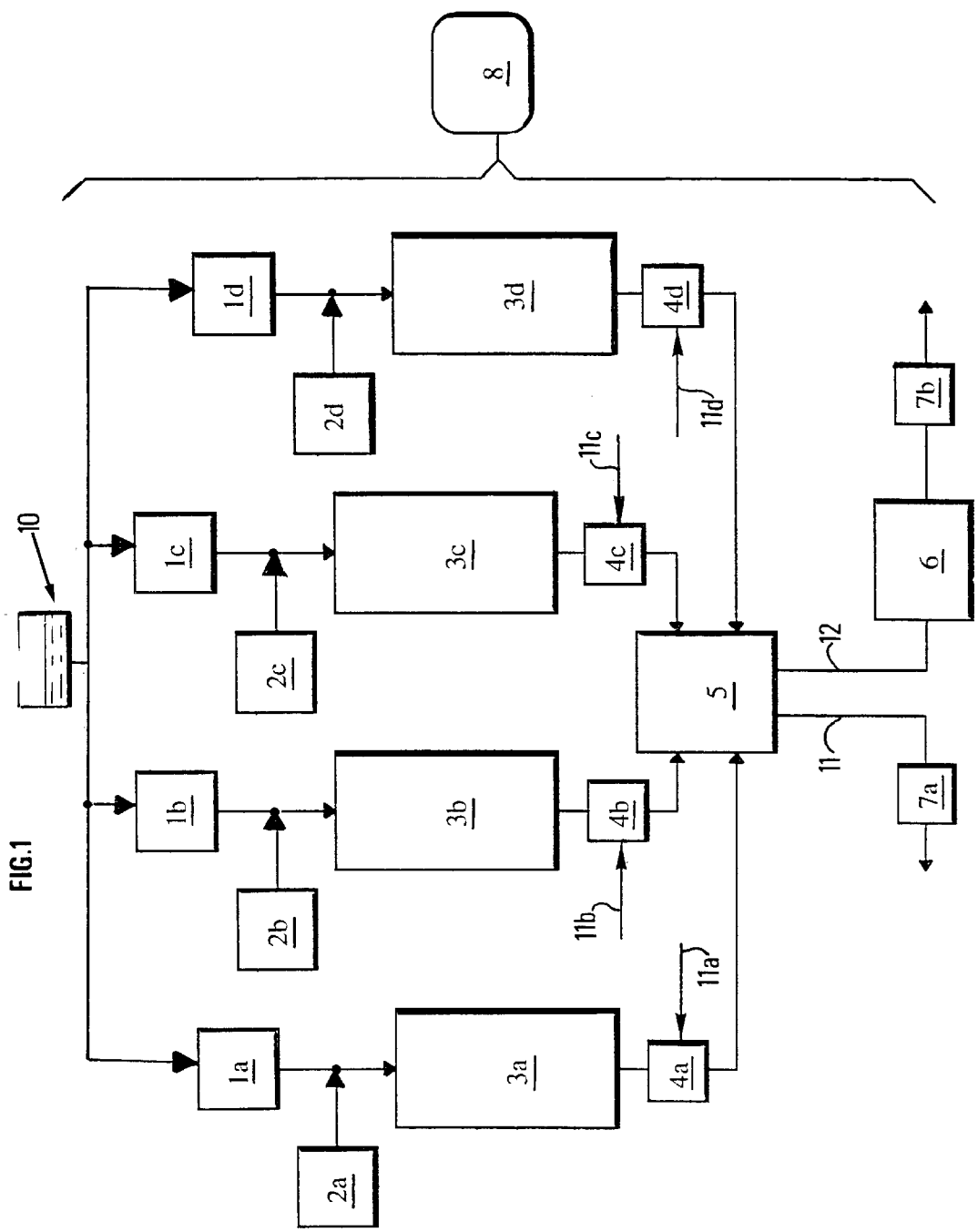
FIG. 1 is the flowsheet of a testing equipment in which the device according to the invention is included.

An example of an equipment advantageously using the distribution device according to the invention, whose flowsheet for four reaction assemblies (suffix a, b, c and d) is given in FIG. 1, consists of the following various subassemblies:

a system for injecting gaseous (2a to 2d) and liquid (1a to 1d) reagents, connected to each reactor 3a, 3b, 3c and 3d, a reaction section (3a to 3d) comprising several microreactors and their heating system, a diluent gas pre-expansion and injection system (4a to 4d) at the outlet of each reactor, the distribution device according to the invention (5) intended for delivery of the effluents coming from each reactor, an analysis system (6) with in-line extraction of the sample to be analyzed and complete expansion (7b), a monitoring/control unit (8) managing the assembly.

Each gaseous reagent injection system (2a to 2d) consists of a pressure reducer-regulator, a safety valve, a pressure detector and a mass flow rate regulator. The gaseous reagent is most often hydrogen. The pressure reducer-regulator allows to maintain a constant pressure at the reactor inlet (ranging between 0 and $1.8 \cdot 10^7$ Pa in relative value) from the available supply pressure. The flow rate range provided by the mass flow rate regulator ranges from 5 to 500 l/h with a 1% relative precision. These regulators can be, for example, models 5850E marketed by BROOKS.

The liquid reagent is injected into each reactor by means of a pump (1a to 1d) that can be a piston type pump with a total volume of at least 500 cm$^3$ such as, for example, the 500 D pumps marketed by ISCO. This type of pump allows high-pressure and high-precision injection, without surges, of very small quantities of liquid (ranging between 0.05 and 100 cm$^3$/h). If the viscosity at ambient temperature of the reagent is not sufficient to allow correct injection, this pump can be equipped with a system allowing to heat it to a moderate temperature (50 to 120° C.). Similarly, the supply vessel 10 of pump 1a (or 1b, 1c, 1d) and the reagent circulation lines between supply vessel 10, the pump and the reactor must be heated for liquid reagents whose viscosity is not sufficient at ambient temperature. Mixing of the liquid and gaseous reagents is performed upstream from the reactor.

In cases where activation of the catalyst requires the presence of a particular chemical compound, it is possible to feed the liquid reagent injection pump from another supply vessel containing this compound dissolved in a solvent.

The inside diameter of the reactors used or microreactors ranges between 0.5 and 3 cm, preferably between 1 and 2 cm for a length ranging between 10 and 50 cm, preferably between 15 and 25 cm. They are arranged vertically in an oven. The direction of flow of the reagents can be ascending or descending. These reactors are made of heat-resisting steel (of Inconel 625 type for example). The cylindrical catalyst bed is located in the central part thereof, it contains between 0.1 and 10 g catalyst. This bed is preceded by a bed of inert material (silicon carbide for example) having the same grain size as the catalyst, whose purpose is to provide preheating and vaporization of the reagents. These reactors are axially equipped with small-diameter thermocouples (0.5 mm for example) allowing to measure the temperature at different points along the longitudinal axis. The heating oven of these reactors consists of at least two (preferably four) zones that are independent as regards temperature control. The first zone corresponds to the reagent preheating and vaporization zone, the second one to the catalyst bed. The presence of various individually controlled zones guarantees isothermal operation of the reactor along the longitudinal axis thereof.

The system (4a to 4d) located at the outlet of each reactor consists of an element (11a to 11d) intended for pre-expansion and controlled flow rate injection of diluent gas into the various reaction product flows (hydrogen or helium for example). The pressure and the temperature are maintained in elements (4a to 4d), distribution device (5) and the product circulation lines connecting reactors (3a to 3d) to analyzer (6) so that the effluent is gaseous to allow proper analysis of the constituents. The pre-expansion overflow type element with a low internal volume allows to lower the pressure of the mixture of reaction products. Expansion to atmospheric pressure of the reaction effluents is provided by complete expansion systems (7a) and (7b) respectively located after distribution device (5) and analyzer (6). The distribution device has, in this example, as many inlets as there are reactors and two outlets 12 and 11, one near to the analyzer, the other near a post-expansion discharge system.

It is important to keep the reaction products in a totally gaseous state in order to allow correct analysis. In fact, the presence of liquid droplets in the sample of these products injected into the analyzer greatly modifies the relative concentrations of the different products. The sample analyzed is then no longer representative of the mixture of reaction products.

This is possible through control and adjustement of the temperature, the total pressure (by means of pre-expansion) and the partial pressures (by means of the dilution ratio, injection 11a–11d). The high-temperature and high-pressure operating conditions of the distribution device can be noted, while inner losses and inner dead volumes likely to distort analyses during the reaction cycle are prevented.

An example of adjustment of these parameters is described hereafter. A reactive mixture of hydrogen and paraffin hydrocarbons containing 11 to 16 carbon atoms (in the proportion of 5 moles hydrogen per mole of hydrocarbons) is converted at 380° C. and 100 bars with a rate of conversion to lighter hydrocarbons of about 50%. At the reactor outlet, the pressure is pre-reduced to 60 bars, the temperature maintained at 230° C. and diluent gas is injected at the reactor outlet. The volume flow rate of this injection is 20 times as great as the flow rate of hydrogen mixed with the reactive hydrocarbons at the reactor inlet. Under such conditions, the quality of the chromatographic analysis is correct. All the reaction products remain in the gaseous state and the sample injected into the chromatographic analyzer is representative of the reaction products.

The distribution device according to the invention (5) comprises a series of valves or shutters allowing the flows coming from the reactors to be sent to either analyzer (6) or a system (7a) intended for direct expansion to the atmospheric pressure. At a given time of the measuring cycles, the outlet way of a reactor is communicated with line 12 of the analyzer, the other ways being then communicated together with line 11 for direct complete expansion. This distribution device 5 is illustrated in FIGS. 4a, 4b, 4c and 4d.

FIG. 4a shows the principle of the distribution device, which can have 2, 4, 6, ... , 2n inlet ways and two outlet ways. The two outlet ways bear reference numbers 20 and 21. In the case shown here, i.e. with 6 inlet ways, the latter are designated by A, B, C, D, E and F. Reference number 22 designates a line sealing element, for example a needle cooperating with a conical seat, activated by a pneumatic or hydraulic piston type operator. The design of the present distribution invention is based on one or more closed-loop lines (23, 24, 25). Each loop is divided into four line sections: 23a, 23b, 23c, 23d; 24a, 24b, 24c, 24d; 25a, 25b, 25c, 25d. Each section is delimited by a sealing element 22. Each loop 23, 24 or 25 comprises two lines for two inlet ways A, B or C, D or E, F. These two inlet lines open each onto two opposite sections, 23a, 23c; 24a, 24c; 25a, 25c. The other two sections communicate each directly with one of the two outlet ways 20, 21.

Thus, if we consider the simplest case of such a distribution device with a single loop (two inlet ways), controlling one or the other of sealing elements (22) delimiting an inlet line allows to select communication of this inlet with one of these two outlets or the other.

If the measuring equipment comprises more than two reactors, the distribution device comprises at least two loops whose outlet lines are connected together, for example by lines 26, 27, as shown in FIG. 4a.

A distribution device of this type allows to use sealing elements 22, for example marketed by NOVA SWISS, which can withstand both high pressures and high temperatures, as it is the case downstream from the reactors.

Furthermore, the configuration of the lines can be such that it constitutes a minimum dead volume, which is essential for the quality of the measurements and of the comparisons between the reaction cycles.

Figure 4C:
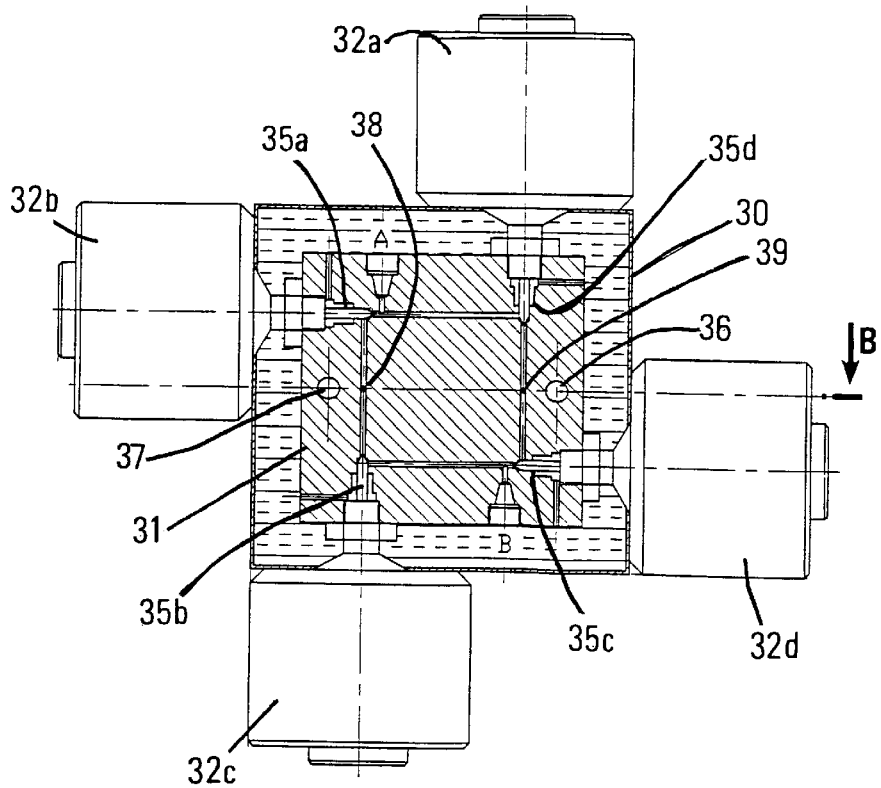

FIG. 4b shows, in side view, an embodiment of the distribution device comprising a housing 30 containing a block 31 wherein the effluent passage lines have been pierced. Reference numbers 32a, b, c and d (FIG. 4c) designate the pneumatic operators, e.g., pneumatic jack operators, which actuate the sealing elements of the various line sections. Space 34 is filled with a thermal insulating material. FIG. 4b shows the distribution device or valve with two loops, i.e., according to the description above, with four inlet ways (for reactors 3a, 3b, 3c and 3d) and two outlets ways. The staggered arrangement of the pneumatic operators allows to have a minimum distance between the two planes containing the two loops. The length of internal lines (26, 27) is thus reduced, which decreases the dead volumes.

FIG. 4c is a cross-section along plane AA (FIG. 4b). The four line sections are made by means of four non-through bores provided in block 31. As shown in the enlarged view of FIG. 4E, inlet ports (35a, b, c, d) are machined to form a sealed seat 40 so as to receive the needle 41 (e.g., conical needle) of the sealing element and the joint stuffing-box type packings. In order to withstand average temperatures of about 250° C., the packings can be made of PEEK (polyetheretherketone). It can be noted that the sealing elements are based on the principle of leakfree elements.

Bores 36 and 37 in block 31 are used for heating and/or regulating elements.

Reference numbers 38 and 39 show the lines connecting the loop sections to the two outlets of the selection valve.

Figure 4D:
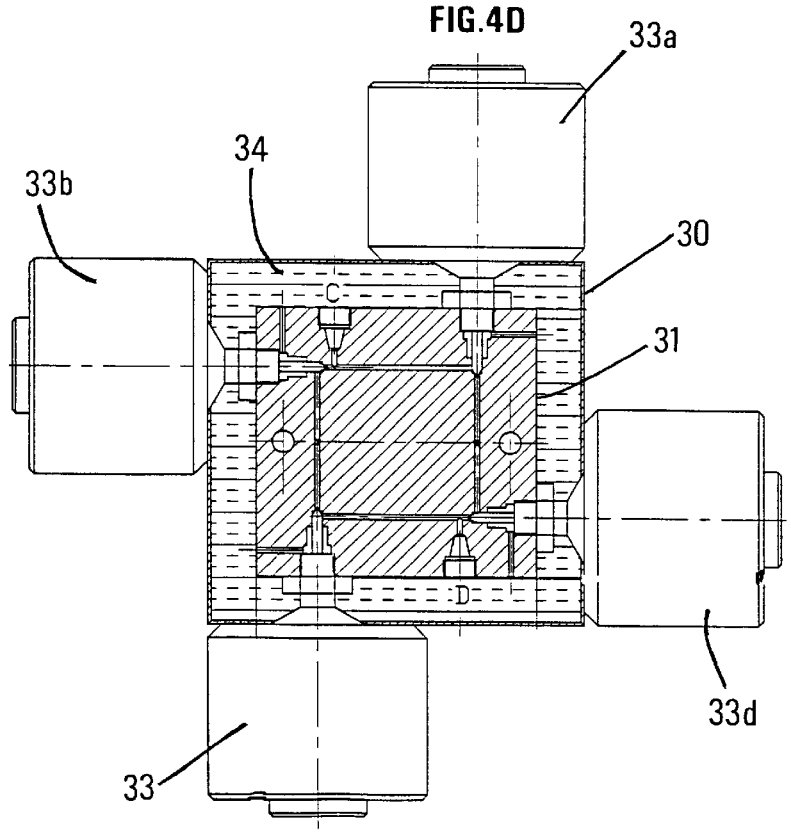

FIG. 4d is a view of section CC in the plane containing the second line loop. The structure is identical to that of the first loop illustrated by FIG. 4c, but the sealing elements are arranged in another direction (at 90°) so that operators 33a, b, c, d are arranged in staggered rows in relation to operators 32a, b, c, d.

Such a distribution device delivering a fluid under pressure (at least 100 bars) and at a high temperature (at least 250° C.) is compact, readily temperature-controlled, of simplified manufacture, and readily automated by means of a single-acting operator. Furthermore, its design readily allows flushing of the communication lines with a neutral gas.

The complete expansion systems (7a) and (7b) (FIG. 1) can be, for example, dome overflow type models marketed by TESCOM.

Analyzer (6) allows detailed analysis of the chemical reaction products. This analyzer is equipped with a valve allowing extraction of samples of these products. This valve, marketed by VALCO for example, is placed under the same temperature and pressure conditions as systems (4a to 4d) and (5). This analyzer can be a gas phase chromatograph, i.e. equipped with one or more chromatographic columns, capillary or not, separating the reaction products by retention time difference. This analyzer can be, for example, a 5890 model marketed by HEWLETT PACKARD or GC2000 marketed by THERMO QUEST.

Control system (8) manages all the various temperature, pressure, flow rate regulations, valves and actuators. This system is built around a SIEMENS automaton S7-400 and a FIX-DEMACS control software marketed by Intellution.

Figure 2:
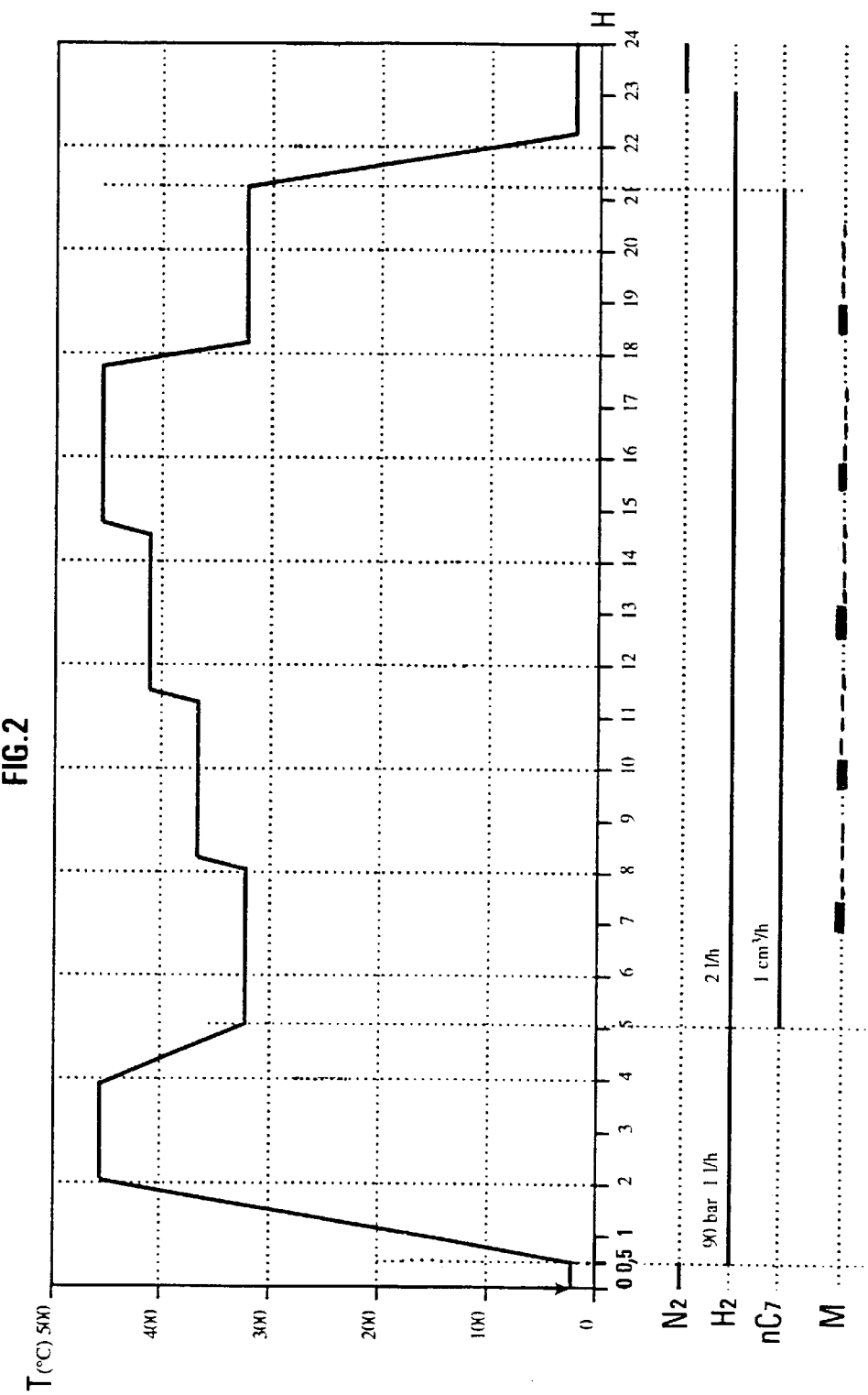
FIG. 2 shows an example of an operational diagram of a reactor.

This control system 8 allows to carry out complete measuring cycles in parallel with the reactors. These cycles typically progress completely autonomously in several successive stages: pressure test of the assembly, flushing with an inert gas, activation of the catalyst if necessary, reaction with performance measurement and finally draining of the installation before it is stopped. An example of a cycle is shown in FIG. 2. The progress of the cycle is shown by the evolution of the temperature T of the reactor as a function of time H. The circuit is flushed with nitrogen from 0 to 0.5 H. The catalyst is activated by injection at a flow rate of 1 l/h at a pressure of 90 b hydrogen from 0.5 to 5 H. The reaction progresses from 5 H to 21 H with the temperature stages shown in FIG. 2, with injection of a nC7 feedstock at 1 cm$^3$/h and hydrogen at 2 l/h. During this cycle, measuring stages M are carried out at regular intervals.

Figure 3:
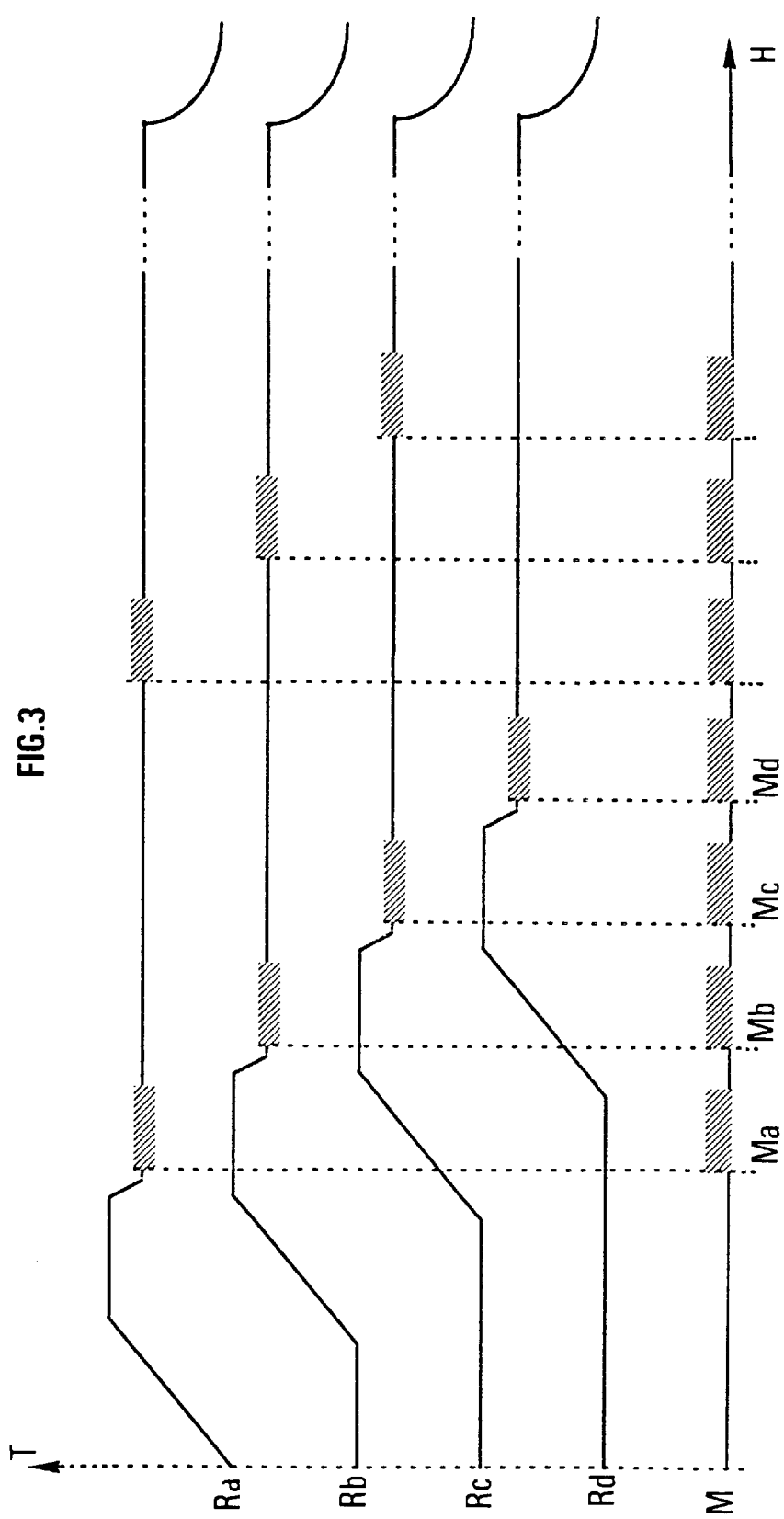
FIG. 3 illustrates the optimized operation of a device with four reactors.

The cycles of each reactor progress simultaneously, which allows several tests to be carried out instead of one. An example of combination of these cycles is given in FIG. 3. The effluents of each reactor Ra, Rb, Rc, Rd are analyzed in turn during stages Ma, Mb, Mc, Md. It can thus be noted that, despite the duration of each test cycle, it is possible to select one reactor after another to perform a measurement on an effluent, which allows to carry out four tests (in the present case) practically during the same time.

EXAMPLES OF USE

1) A hydroconversion catalyst A contains Ni and Mo as the active metal phase and a zeolite of Y structure as the acid phase. Four samples (1.2 g) of this catalyst are placed in the reactors of the equipment according to the invention. Normal hexadecane to which 0.4% by weight of sulfur-containing compound dimethyldisulfide and hydrogen have been added are used as the reagents. The operating conditions selected, identical for each reactor, are as follows:

inlet pressure: 1.5 $10^7$ Pa
flow rate of reagent $nC_{16}H_{34}$: 0.745 g/h
flow rate of gaseous reagent $H_2$: 0.80 l/h
temperature: 340° C.

The reaction products are expanded to 5.0 $10^6$ Pa at the reactor outlet. Dilution hydrogen is injected at a flow rate of 40 l/h at the outlet of each reactor and the temperature of the zones through which these reaction products flow between the outlet of the reactors and the analyzer is maintained at 240° C.

Prior to the reaction stage proper, an activation stage referred to as catalyst sulfurization is carried out. This treatment consists in injecting into the reactor the sulfur-containing compound dimethyldisulfide dissolved (1.0% by weight) in normal heptane. The other conditions of this treatment are as follows:

inlet pressure: 6.0 $10^6$ Pa
flow rate of $nC_7H_{16}/C_2H_6S_2$: 0.650 g/h
flow rate of gaseous reagent $H_2$: 0.60 l/h
temperature: 350° C.
duration: 2 h.

During the reaction stage, analyses are carried out on each reactor every 6 hours for 180 hours, which eventually amounts to more than 120 analyses. The analyzer used is a gas phase chromatograph equipped with a 50-m long and 0.2-mm diameter apolar capillary column of PONA type and with a flame ionization detector. The areas of the chromatographic peaks are used to calculate the concentrations in the various reaction products (normal hexadecane, isomers of normal hexadecane and lighter hydrocarbons). The conversion of normal hexadecane is calculated from these data.

The results obtained with all the measurements and expressed as average values are as follows:

| Reactor No. | 1 | 2 | 3 | 4 | |
|---|---|---|---|---|---|
| Number of analyses | 28 | 30 | 27 | 30 | |
| Average conversion | 62.1 | 62.3 | 61.9 | 62.1 | % by weight |
| Standard deviation | +/−0.7 | +/−0.6 | +/−0.6 | +/−0.7 | % by weight |

These measurements, performed in the four reactors under the same conditions and with the same catalyst, allow to assess the global precision of the equipment in terms of repeatability. The relative precision of a conversion value provided by the equipment according to the invention is close to 1 to 2% (ratio between the standard deviation and the average conversion).

2) Three hydroconversion catalysts B, C and D contain all Ni and Mo as the hydrogenizing active phase and a zeolite of Y structure as the acid phase, but in different proportions in relation to catalyst A. Fast evaluation of these four samples is sought in terms of activity and of global selectivity. The reagent selected therefore is normal hexadecane to which 0.4% by weight of sulfur-containing compound dimethyldisulfide $C_2H_6S_2$ has been added. The four reactors of the plant are each supplied with 1.2 g of these catalysts. The operating conditions selected for each reactor are as follows:

inlet pressure: $9.5 \cdot 10^6$ Pa flow rate of reagent $nC_{16}H_{34}$: 0.745 g/h flow rate of gaseous reagent $H_2$: 0.80 l/h.

The performances are measured for four successive increasing temperature stages 320, 340, 360 and 370° C. Each stage lasts for 2 h. A fifth and last temperature stage is performed at 320° C. to assess the possible deactivation of the catalysts. Analyses are carried out 1 h30 after the beginning of each temperature stage.

The reaction stage is preceded by a sulfurization similar to the stage of example 1. The temperature, pressure and diluent gas flow adjustments at the outlet of the reactors are identical to those of example 1.

All these operating conditions are programmed in the automaton. The corresponding cycles are close to the examples shown in FIGS. 2 and 3. The total duration of a cycle is slightly less than 24 h. During this time, there is no intervention by the operator.

The results obtained are given in the table hereafter:

| Catalyst | | A | B | C | D | |
|---|---|---|---|---|---|---|
| Temperature (° C.) | | | | | | |
| 320 | nC16 conversion | 34.8 | 18.1 | 3.3 | 27.0 | % by weight |
| | isomerization | 24.5 | 17.2 | 4.1 | 12.3 | % |
| | cracking | 75.5 | 82.8 | 95.9 | 87.7 | % |
| 340 | nC16 conversion | 62.1 | 43.0 | 8.5 | 51.3 | % by weight |
| | isomerization | 43.2 | 37.4 | 10.1 | 20.0 | % |
| | cracking | 56.8 | 62.6 | 89.9 | 80.0 | % |
| 360 | nC16 conversion | 90.2 | 62.1 | 20.0 | 75.0 | % by weight |
| | isomerization | 39.5 | 48.5 | 22.5 | 26.9 | % |
| | cracking | 60.5 | 51.5 | 77.5 | 73.1 | % |
| 380 | nC16 conversion | 98.7 | 84.6 | 37.4 | 93.2 | % by weight |
| | isomerization | 30.2 | 49.1 | 40.1 | 32.6 | % |
| | cracking | 69.8 | 50.9 | 59.9 | 67.4 | % |
| 320 | nC16 conversion | 34.5 | 17.9 | 3.2 | 27.0 | % by weight |
| | isomerization | 24.8 | 17.3 | 4.0 | 12.9 | % |
| | cracking | 75.2 | 82.7 | 96.0 | 87.1 | % |

The activity is represented by the conversion level of the reagent normal hexadecane for a given temperature. The selectivities for the reactions of isomerization of normal hexadecane to iso hexadecane and of cracking of normal hexadecane to lighter hydrocarbons are calculated by dividing the isomerization and cracking products yields by the conversion.

The results clearly show great differences between these catalytic solids. Sample A is the most active whatever the temperature, whereas sample C is the most selective. The relative precision obtained in example 1 is amply sufficient to determine the differences observed.

Applied to selection of catalytic solids, the equipment and the method using the distribution device according to the invention thus allow fast, parallel, and high-precision evaluation of several catalytic solids.

What is claimed is:

1. A distribution device notably intended for a gaseous effluent produced by a chemical reaction, comprising at least two inlet ways and two outlet ways, characterized in that it comprises at least one closed-loop circuit divided into four sections by four controlled sealing elements, in that each one of said four ways communicates with a single section so that the inlet ways are connected to two opposite sections and said outlet ways are connected to the other two sections.

2. A device as claimed in claim 1, comprising two closed-loop lines and said outlet ways communicate together two by two so as to form a distribution device with four inlet ways and two outlet ways.

3. A device as claimed in claim 1, wherein each of said sealing elements comprises a conical needle cooperating with a sealed seat.

4. A device as claimed in claim 1, wherein each of said sealing elements is activated by a pneumatic jack operator.

5. A device as claimed in claim 1, wherein said closed-loop circuit comprises four rectilinear lines arranged in the shape of a quadrilateral, said sealing elements being arranged substantially at the four corners of said quadrilateral.

6. A device as claimed in claim 1, wherein the sealing elements are suited to an effluent pressure and temperature that reach 250 b and 400° C. respectively.

7. Equipment intended for measurement on an effluent resulting from a chemical reaction taking place in a reactor containing a catalyst, and comprising:

at least two reactors, analysis and measuring means intended for said effluent, means intended for automatic monitoring and control of the chemical reaction and of the analysis and measurement cycle, and the distribution device as claimed in claim 1, said distribution device supplying said analysis and measuring means alternately with the effluents from the two reactors in order to perform two analysis and measurement cycles on two reactions progressing in parallel.

\* \* \* \* \*